United States Patent [19]

Eibl

[11] Patent Number: 4,749,805
[45] Date of Patent: Jun. 7, 1988

[54] PHOSPHOLIPID-LIKE COMPOUNDS

[75] Inventor: Hansjörg Eibl, Bovenden, Fed. Rep. of Germany

[73] Assignee: Max-Planck-Gesellschaft Zur Foerderung der Wissenschaften e.V., Goettingen, Fed. Rep. of Germany

[21] Appl. No.: 13,145

[22] Filed: Feb. 11, 1987

Related U.S. Application Data

[63] Continuation of Ser. No. 682,812, Dec. 18, 1984, abandoned, which is a continuation of Ser. No. 960,398, Nov. 13, 1978, abandoned.

[30] Foreign Application Priority Data

Nov. 24, 1977 [DE] Fed. Rep. of Germany ....... 2752553

[51] Int. Cl.$^4$ ................................................ C07F 9/10
[52] U.S. Cl. ..................................... 558/169; 260/403
[58] Field of Search ........................ 260/403; 558/169

[56] References Cited

U.S. PATENT DOCUMENTS 4,119,714 10/1978 Kay et al. ............................ 558/169

FOREIGN PATENT DOCUMENTS 2752125 5/1979 Fed. Rep. of Germany ...... 558/169
2752553 5/1979 Fed. Rep. of Germany ...... 558/169

OTHER PUBLICATIONS

Kosolapoff et al., "Organic Phosphorus Compounds", vol. 6, (1974), p. 227.
Wagner et al., "Synthetic Organic Chemistry," (1953), pp. 665–666.

*Primary Examiner*—Anton H. Sutto
*Attorney, Agent, or Firm*—Felfe & Lynch

[57] ABSTRACT

Compounds related to phospholipids and a method for their preparations.

6 Claims, No Drawings

PHOSPHOLIPID-LIKE COMPOUNDS

This application is a continuation of Ser. No. 682,812, filed 12/18/84, which is a continuation of Ser. No. 960,398, filed 11/13/78, both now abandoned.

BACKGROUND

The invention relates to a new class of compounds closely related to the phospholipids, and to a method for their preparation as well as to their use.

In hybridization experiments with vegetable as well as with animal cells, it is very difficult to achieve the combining of different cells, since all cells as a rule are negatively charged and have negative surface charges of the order of 30 to 35 millivolts. If it would be possible not only to neutralize cells but even to reverse their charges, it would be possible in this manner to introduce an artificial sexuality and thus obtain specific fusions between two different cells, e.g., fusions of protoplasts.

Unspecific fusions of protoplasts are already known. In unspecific fusions between two negatively charged protoplasts A and B, however, it is mainly homologous fusions that are obtained:

| | | |
|---|---|---|
| A + A | ⎫ | homologous |
| B + B | ⎬ | |
| A + B | = | heterologous. |

The term, specific fusion, is used to refer to a fusion between A and B. The specificity can be achieved by introducing an artificial sexuality by the production of an excess positive charge on protoplast A, which is then fused with the negatively charged protoplast.

There is a need, therefore, for means and methods which will permit the reversal of charges on cell surfaces. Furthermore, there is a general need for means which are suitable for modifying the properties of cell membranes, especially by modifying the charge, and it is especially important that such compounds be biologically degradable.

THE INVENTION

It is therefore the object of the invention to create a new class of compounds which on the basis of their chemical structure have a special affinity for the cell wall, and therefore are suitable for the modification of cell membranes and especially for the reversal of their charge, and which furthermore can also be degraded by the cell.

This object is achieved in accordance with the invention by the creation of compounds of General Formula I:

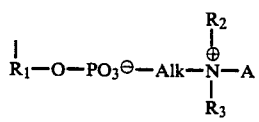
                I wherein Alk represents a straight-chain, branched or cyclic alkyl group having 2 to 12 carbon atoms,
A represents the group:

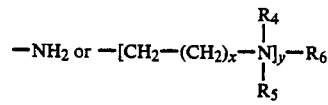

$R_1$ represents the moiety of a univalent or polyvalent aliphatic primary or secondary alcohol whose additional OH groups, if any, are in the esterified or etherified state and the ester or ether groups contain 1 to 26 carbon atoms and, in some cases, one or more carbon multiple bonds, wherein $R_1$ contains a total of at least 6 carbon atoms, $R_1$, $R_4$ and $R_6$ represent hydrogen or an alkyl group having 1 to 4 carbon atoms, $R_3$ and $R_5$ represent hydrogen or an alkyl group having one to four carbon atoms or a free pair of electrons, x and y independently of one another represent the number 1, 2, 3, 4 or 5.

If $R_1$ represents the moiety of a univalent alcohol, the esterified or etherified hydroxyl groups can also be joined together in ring structures, for example by etherification with a ketone, such as dipentadecylketone. In this case, where the hydroxyl groups are adjacent one another, the result will be five-member rings containing two oxygen atoms.

The ether and ester groups can be saturated or unsaturated, straight-chain, branched or cyclic alkyl groups, aryl groups, especially phenyl and naphthyl groups, as well as aralkyl groups, in which the sum of the carbon atoms in the aryl moiety and in the alkyl moiety or moieties amounts to as much as 26 carbon atoms. Of the ester or ether groups on the moiety $R_1$ those are preferred in which the alkyl, aryl or aralkyl groups have 8 to 22 carbon atoms. Especially preferred are compounds in which $R_1$ is derived from propane, diol or glycerol. examples of other suitable polyvalent alcohols are erythritol, pentitols, hexitols etc.

Furthermore preferred in the scope of the invention are those compounds in which $R_2$, $R_3$, $R_4$, $R_5$ and $R_6$ represent alkyl groups, such as methyl, ethyl, propyl, isopropyl, n-butyl, isobutyl or tertiary butyl groups.

The method of the invention for the preparation of the new compounds described above is characterized by the fact that (a) a compound of the General Formula II

            II is reacted in a known manner with POCl₃, (b) the reaction product of step (a) is reacted in a known manner with a compound of the General Formula III

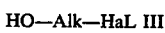   III in which Hal represents Cl, Br or I, (c) The reaction product of Step (b) is reacted with a compound of the General Formula IV

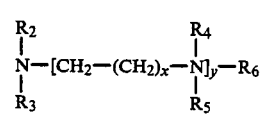     IV or with hydrazine, $R_1$, $R_2$, $R_4$, $R_5$, $R_6$, Alk, X and y having the meaning given in claim 1, and, in some cases, (d) the obtained compound of General Formula I, in which $R_3$ and/or $R_5$ represent a free electron pair, is peralkylated with an alkylating agent.

Of the compounds of General Formula III, the bromine-containing compounds are preferred. With regard to the moiety Alk, those having 2 to 4 carbon atoms are preferred in the case of the straight-chain and branched moieties, and those having six carbon atoms are preferred in the case of the cyclic groups. Especially preferred is an alkyl group having two carbon atoms.

The reaction of phosphorus oxychloride with the compound of General Formula II in Step (a) is preferably performed in an inert organic solvent. Examples of suitable solvents are halogenated hydrocarbons such as chloroform and carbon tetrachloride, aromatic hydrocarbons such as benzene or toluene, and aliphatic hydrocarbons such as petroleum ethers and the like. Also suitable are cyclic organic solvents such as tetrahydrofuran. Trichloroethylene and tetrahydrofuran are preferred, since then the salts that develop, such as triethylamine hydrochloride, have a very low solubility and therefore they precipitate and can easily be separated by filtration. The reaction is to be performed with the exclusion of moisture to the greatest possible extent. Suitable temperatures range between −10° and 50° C., preferably between 10° and 30° C. Depending on the substances and solvents used, however, temperatures higher or lower than these limits can be used in many cases.

The reaction is performed preferably in the presence of an inert organic base, such as triethylamine, pyridine or quinoline.

It is desirable to dissolve the phosphorus oxychloride in the inert solvent and add the base. Then the compound of General Formula II, preferably also dissolved in an inert solvent, is added, preferably drop by drop, with stirring. Since the reactions take place in a smooth and well-defined manner, the temperature can be selected from case to case such that the reaction will have ended directly after the drop-by-drop addition, as can easily be determined by thin-layer chromatography.

Step (b) takes place smoothly if the product of Step (a) is mixed with the compound of General Formula III. Preferably, a solution of the compound of General Formula III is added to the reaction mixture in the presence of an organic base, such as triethylamine. Preferably the reaction takes place at temperatures between 20° and 60° C. with the use of tetrahydrofuran as solvent. Depending on the conditions applied, the reaction time is generally between about 20 and 120 minutes.

Under the preferred conditions, the hydrohalide of the base precipitates and is removed. To obtain the best yields, the hydrochloride is washed and the wash liquid is recycled to the reaction solution. Then the solvent is removed. The residue is then dissolved, if desired, in tetrahydrofuran and hydrolyzed with a weakly alkaline aqueous solution, such as sodium bicarbonate in water for example, the pH being preferably maintained between 5 and 7. Then it is extracted with an organic solvent such as diisopropyl ether or chloroform. The sodium salts of the alkyl phosphatide acids are thus obtained, which can easily be recrystallized.

Alternatively, the reaction products of Step (b) can also be prepared by cleaving corresponding ring compounds of the General Formula I described in German Patent... (Patent application of same applicant, filed on Nov. 22, 1977, under internal No. GI 457), using alkyl halides as described therein.

The reaction in Step (c), that is, the reaction of the product of Step (b) with the amino base, is likewise generally performed in polar solvents, such as chloroform, primary, secondary or tertiary alcohols, dimethylformamide, acetonitrile, nitromethane or water or mixtures thereof, for example. Depending on the sensitivity of the starting substances, any temperature between the fixed point and the boiling point of the solvent or solvent mixture can be used. Preferably, the reaction takes place at temperatures between room temperature and the boiling point of the solvent. The reactions are thus completed, as a rule, in from 2 to 8 hours. The reaction product is then isolated and can be recrystallized. Chromatographic purification is also possible. The yields generally amount to more than 50% of the theory with respect to diglyceride starting product. The amination method described in Example 1, step (c), has proven very practical for amination with monofunctional bases, such as trimethylamine, triethylamine, dimethylamine, methylamine and ammonia, resulting in the formation of neutral phospholipids.

The high yields of desired product which are achieved are surprising, because in view of the many functional groups in the reactants, it could not have been anticipated that the reaction in the desired direction could be effected easily.

Step (d), i.e., the peralkylation of the product of Step (c), makes it possible to increase the alkalinity of the compound, if desired, if a pH value of more than 6 is desired for the second or the next nitrogen in the molecule. This is important when the compounds are to be used in a neutral or alkaline medium rather than an acid one. The alkylation is best performed in a known manner by reaction with methyl iodide or other suitable alkylating agents under conditions familiar to a person skilled in the art.

Preferably, however, the alkylation is performed at pH values between 7 and 11, with an alkylating agent in tetrahydrofuran in the presence of a dilute aqueous alkali carbonate solution. With special preference, 0.5×molar sodium bicarbonate solution is used, and methyl iodide serves as a methylating agent. This new embodiment of the alkylation takes place especially smoothly and rapidly and is also generally suitable for the alkylation of nitrogen atoms such as those occurring in cephalin.

An apparently similar procedure is known, but in it the product to be alkylated is treated in tetrahydrofuran with solid sodium carbonate. In this case the reaction takes about two weeks to complete, and by-products develop which necessitate an expensive refining procedure.

As previously stated, the compounds of the invention are distinguished by their ability to modify cell membranes. In particular, they can change the charge on the cell surfaces, and thus make it possible to perform cell fusions by bringing together normal cells with reverse-charged cells which can easily be obtained by treatment with the compounds of the invention. This can be utilized for the development, for example, of new plant hybrids.

Furthermore, the compounds of the invention have valuable pharmacological properties, because the compounds analogous to lecithin are strongly surface active substances which alter permeability conditions in biological membranes and therefore are capable both of penetrating the cell wall and of permitting other medicaments or biologically active substance to gain entry into the cell membrane, the compounds of the invention forming vesicles in which the substances to be transported are enclosed. Also, the receptors on the cell walls, such as for example the hormone receptors, can be specifically altered, thereby increasing or decreasing, as desired, the ability of the cell walls to absorb hormones and other compounds. In addition, they have immunity stimulating properties, and they can be expected to have an effectiveness against infections, because it is possible by altering the permeability conditions at the cell membranes to reduce vulnerability to microorganisms and viruses.

Since the compounds of the invention have both lipophilic and hydrophilic groups as well as acid and basic groups in the same molecule, they are good emulsifiers. Due to their close relationship to natural phosphatides, they are biologically degradable and therefore they can also be used as emulsifiers in foods and in detergents and the like.

EXAMPLES

The following examples will serve to further explain the invention.

A. The Process of the Invention, Generally

Example 1

Step a 10 ml of trichlorethylene and 6.6 g of $POCl_3$ (0.044 moles) are treated in an ice bath at 0° to 5° C. with 0.04 mole of a primary or secondary alcohol of General Formula II, dissolved in 40 ml of trichlorethylene and 9 g of triethylamine. If the alcohol is a diacyl glycerol, the acylation mixture is treated successively with 9 g of triethylamine in 10 ml of trichlorethylene and then immediately with the diacyl glycerol in 30 ml of trichlorethylene, so as to prevent acyl migration. 25 ml of toluene is used for the washing. The ice bath is replaced by a water bath at 20° C. The reaction ends 20 minutes later at 20° C.

Step b

At 20° C., 0.048 mole of Compound III, dissolved, for example, in 75 ml of tetrahydrofuran and 13 g of triethylamine are added to the reaction mixture of Step a and 25 ml of tetrahydrofuran is used for the washing. After 20 minutes at 35° C., the reaction has ended. Filtration is performed, followed by a washing in 50 ml of toluene and concentration. The hydrolysis is performed by the successive addition of 30 ml of ice water, two minutes later 30 ml of 1M sodium acetate, and another two minutes later 90 ml of tetrahydrofuran. Twelve hours later the hydrolysis has ended. Virtually only a single product develops.

Step c

B.

0.04 mole of the product of step b (β-bromoethyl ester) is dissolved in 90 ml of $CHCl_3$, and 150 ml of isopropanol and 200 ml of 40% N,N,N,N-tetramethylethylenediamine in water are added. Here the other compounds of Formula IV, for example diaminoethane, diaminopropane etc., or hydrazine, can be used accordingly. At 50° C. the reaction is completed in 24 hours. After the addition of toluene, the mixture is concentrated until the aqueous phase remains, and the product is precipitated by acetonitrile. The purification is performed by chromatography on silica gel.

Example 2

Transformation of β-Bromoethyl Ester with Diethylene Triamine

β-Bromoethyl ester of Example 1 (0.04 mole) is dissolved in 90 ml of $CHCl_3$, and is treated with 150 ml of isopropanol and with 200 ml of 40% diethylene triamine. Accordingly, other polyamines can be used here, such as for example triethylene tetramine and tetraethylene pentamine. After the addition of toluene, the mixture is concentrated until the aqueous phase remains, and the product is precipitated with acetonitrile. Purification is performed by chromatography on silica gel.

Example 3

Permethylation of the Amino Functions 0.01 mole of the aminated product, for example 7.9 g of Compund 5, is dissolved in 50 ml of tetrahydrofuran, and treated with 50 ml of 1M $NaHCO^3$ (8.4 g dissolved in 100 ml of $H_2O$. 30 g of methyl iodide is added with stirring. The reaction is complete after 60 minutes. Extraction is performed with chloroform and the pure product is obtained; occasionally, chromatography is also necessary for purification.

The following compounds have been prepared by the methods of Examples 1 to 3:

Example 4

1,2-Dipentadecylketone-glycerol-3-phosphoryl-(N-ethylamino)ethanolamine, $C_{38}H_{79}N_2O_6P$ (691.0)

Calculated: C 66.05%; H 11.52%; N 4.05%; P 4.48%; Found: C 66.11; H 11.63; N 4.03; P 4.70

Example 5

Stearoyl-propanediol-(1,3)-phosphoryl-(N,N-dimethyl-N-[N',N'-dimethyl]-ethylamino)-ethanolammonium, $C_{29}H_{61}N_2O_6P$ (562.8)

Calculated: C 61.67%; H 10.89%; N 4.96%; P 5.48%; Found: C 60.41; H 10.73; N 4.60; P 5.45

Example 6

Palmitoyl-propanediol-(1,3)-phosphoryl-(N,N-dimethyl-N-[N',N'-dimethyl]-ethylamino)-ethanolammonium, $C_{27}H_{57}N_2O_6P$, (536.7).

Proven by thin layer chromatography compared with the product of Example 5.

Example 7

Oleoyl-propanediol-(1,3)-phosphoryl-(N,N-dimethyl-N-[N',N'-dimethyl]-ethylamino)-ethanolammonium, $C_{29}H_{59}N_2O_6P$ (562.8)

Proven by thin layer chromatography compared with the product of Example 5.

Example 8

1,2-Dipalmitoyl-sn-glycerol-3-phosphoryl-N,N-dimethyl-N-[N',N'-dimethyl]-ethylamino)-ethanolammonium, $C_{43}H_{87}N_2O_8P$ (791.2)

Calculated: C 65.28%; H 11.09%; N 3.54%; P 3.92%; Found: C 64.99; H 11.02; N 3.40; P 4.01

Example 9

1,3-Dipalmitoyl-glycerol-2-phosphoryl-(N,N-dimethyl-N-[N',N'-dimethyl]-ethylamino)-ethanolammonium, $C_{43}H_{87}N_2O_8P$ (791.2)

Proven by thin layer chromatography compared with the product of Example 8.

Example 10

1,2-Dimyristoyl-sn-glycerol-3-phosphoryl-(N,N-dimethyl-N-[N',N'-dimethyl]-ethylamino)-ethanolammonium, $C_{39}H_{79}N_2O_8P$ (735.0)

Proven by thin layer chromatography compared with the product of Example 8.

Example 11

1,3-Dimyristoyl-glycerol-2-phosphoryl-(N,N-dimethyl-N-[N',N'-dimethyl]-ethylamino)-ethanolammonium, $C_{39}H_{79}N_2O_8P$ (735.0)

Proven by thin layer chromatography compared with the product of Example 8.

Example 12

1,2-Dihexadecyl-glycerol-3-phosphoryl-(N,N-dimethyl-N-[N',N'-dimethyl]-ethylamino)-ethanolammonium, $C_{43}H_{91}N_2O_6P$ (763.2)

Calculated: C 67.67%; H 12.02%; N 3.67%; P 4.06%; Found: 66.93; H 11.87; N 5.50; P 4.11

Example 13

1,2-Dihexadecyl-glycerol-3-phosphoryl-ethanolhydrazine, $C_{37}H_{79}N_2O_6P$ (679.0)

Calculated: C 65.45%; H 11.73%; N 4.13%; P 4.56%; Found: C 64.94; H 11.80; N 3.98; P 4.61

Example 14

1,2-Dimyristoyl-sn-glycerol-3-phosphoryl-(N-hexylamino)-ethanolamine, $C_{43}H_{87}N_2O_8P$ (791.2)

Proven by thin layer chromatography in comparison with the product of Example 10.

Example 15

1,2-Dimyristoyl-sn-glycerol-3-phosphoryl-(N-ethylamino)-hexanolamine, $C_{43}H_{87}N_2O_8P$ (791.2)

Proven by thin layer chromatography in comparison with the product of Example 10.

Example 16

1,3-Dipalmitoyl-glycerol-2-phosphoryl-(N-[N'-ethylamino]-ethylamino)-ethanolamine, $C_{41}H_{84}N_3O_8P$ (778.1)

Calculated: C 63.29%; H 10.88%; N 5.40%; P 3.98%; Found: C 63.11; H 10.64; N 5.60; P 4.00

Example 17

Stearoyl-propanediol-(1,3)-phosphoryl-(N,N-dimethyl-N-[N',N',N'-trimethyl]-ethanolammonium chloride, $C_{30}H_{64}ClN_2O_6P$ (615.3)

Calculated: C 58.56%; H 10.49%; N 4.55%; P 5.03%; Found: C 60.11; H 10.97; N 4.85; P 5.01

Example 18

Palmitoyl-propanediol-(1,3)-phosphoryl-(N,N-dimethyl-N-[N',N',N'-trimethyl]-ethanolammonium chloride, $C_{28}H_{60}ClN_2O_6P$ (587.2)

Proven by thin layer chromatography.

Example 19

1,2-Dipalmitoyl-sn-glycerol-3-phosphoryl-(N,N-dimethyl-N-[N',N',N'-trimethyl]-ethylammonium chloride, $C_{44}H_{90}ClN_2O_8P$ (841.7) Calculated: C 62.79%; H 10.78%; N 3.33%; P 3.68%; Found: C 63.33; H 10.95; N 3.60; P 4.11

Example 20

Fusion of Protoplasts

Protoplasts of plants of higher cells were prepared by the method of Takebe, Otsuki and Aoki, Plant Cell Physiol. 9, 115 (1968). $5 \times 10^5$ to $10^6$ protoplasts per ml were let stand for 20 minutes in a buffer prepared with 1 mM of the phospholipid of Formula I of the invention, 0.025M of citrate (pH 5.8), 0.05M of $CaCl_2$ and 0.7M of mannitol, and then centrifuged. The supernatant liquid is decanted and the precipitate is placed in 1 ml of a solution containing 0.05M of $CaCl_2$ and 0.7M of mannitol, on a Petri dish (Greiner Nürtingen) whose surface had been treated in a known manner to improve the adherence of protoplasts. After 30 seconds, untreated protoplasts were added. Within 1 to 2 minutes, specific fusions can be observed under the microscope.

I claim:
1. Compounds of the formula

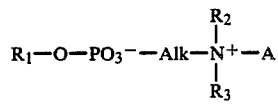

wherein
Alk represents an alkyl group having 2 to 12 carbon atoms, A represents the group

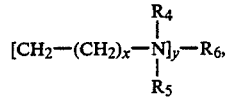

$R_1$ represents a univalent or polyvalent primary of secondary alcohol of at least 6 carbon atoms whose additional OH groups, if any are substituted by a moiety selected from the group consisting of ester and ether moieties, said ester and ether moieties comprising from 1 to 26 carbon atoms;

$R_2$, $R_4$, and $R_6$ represent hydrogen or an alkyl group of 1 to 4 carbon atoms;

$R_3$ and $R_5$ represent a hydrogen atom or an alkyl group having 1 to 4 carbon atoms or a free electron pair, and x and y represent a number from 1 to 5.

2. Compound of claim 1 characterized in that $R_1$ is derived from propanediol or glycerol.

3. Compounds of claim 1, wherein $R_1$ contains additional OH groups, said OH groups being in the esterified or etherified state, said ester or ether groups containing 1 to 26 carbon atoms.

4. Compound of claim 3, characterized in that the ester or ether groups contain alkyl, aryl, or aralkyl groups having 8 to 22 carbon atoms.

5. Compounds of claim 3, wherein said ester or ether groups contain at least one carbon—carbon double bond.

6. 1,2-Dihexadecyl-glycerol-3-phosphoryl-(N,N-dimethyl-N-[N',N'-dimethyl]-ethylamino)-ethanolammonium.

* * * * *